United States Patent [19]

Larue et al.

[11] Patent Number: 5,583,200
[45] Date of Patent: Dec. 10, 1996

[54] STABILIZED COMPOSITION OF TROPONIN FOR IMMUNOASSAYS AND PROCESS FOR STABILIZING TROPONIN FOR IMMUNOASSAYS

[75] Inventors: Catherine Larue, Montpellier; Pierre-Yves Marquet, Meyzieu, both of France

[73] Assignee: Pasteur Sanofi Diagnostics, Marnes-La-Coquette, France

[21] Appl. No.: 536,361

[22] Filed: Sep. 29, 1995

Related U.S. Application Data

[63] Continuation of Ser. No. 197,298, Feb. 16, 1994, abandoned.

[30] Foreign Application Priority Data

Feb. 23, 1993 [FR] France .................................. 93 02067

[51] Int. Cl.$^6$ ..................... C07K 14/435; C07K 14/47; G01N 33/53; G01N 33/531
[52] U.S. Cl. ..................... 530/350; 435/7.1; 435/960; 435/967; 530/841
[58] Field of Search ..................... 530/350, 841; 514/21; 435/7.1, 7.4, 960, 967

[56] References Cited

U.S. PATENT DOCUMENTS 5,290,678  3/1994  Jackowski ..................... 435/7.4

OTHER PUBLICATIONS

Ingraham, R. H. and Al., "Binary Interactions of Troponin Subunits", abstracts, *The Journal of Biological Chemistry*, vol. 259, No. 15, Aug. 10, 1984, pp. 9544–9548.

Cummins, B. and Al., "Cardiac-specific troponin–I radioimmunoassays in the diagnosis of acute myocardial infarction," *American Heart Journal*, vol. 113, No. 6, 1987, pp. 1333–1344.

Katus, H. A. and Al., "Diagnostic Efficiency of Troponin T Measurements in Acute Myocardial Infraction," *Circulation*, vol. 83, No. 3, Mar. 1991, pp. 902–912.

Syska, H. and Al., "A new method of preparation of troponin I (inhibitory protein) using affinity chromatography, Evidence for three different forms of troponin I in striated muscle," *Febs Letters*, vol. 40. No. 2, Apr. 1974, pp. 253–257.

Thulin, E. and Al, "Purification of Rabbit Skeletal Muscle Troponin C," *ACTA Chemica Scandinavica*, vol. B42, 1988, pp. 211–215.

Remingtons Pharmaceutical Science, 18th ed. 1565–1567 1990.

Chong et al. "A New Heterobifunctional Cross–linking Reagent for the Study of Biological Interactions between Proteins" J. Biol. Chem. 256(10) 5071–5076 1981.

Cheung et al. "Interactions of Troponin Subunits: Free Energy of Binary and Ternary Complexes" Biochemistry 26(18) 5504–5907 1984.

McCubbin et al. "Physicochemical Studies on the Interaction of the Calcium–Binding Protein (Troponin C) with the Inhibitory Protein (Troponin I) and Calcium Ions" Biochem. 13(13) 2689–2694 1974.

Horwitz et al. "Interaction of Troponin Subunits" J. Biol Chem 254(2) 350–355 1979.

Head et al. "The Interaction of the Calcium–Binding Protein (Troponin C) with Bivalent Cations and the Inhibitory Protein (Troponin I)" Biochem J. 137 145–154 1974.

Larue, Catherine, et al., "New Monoclonal Antibodies as Probes for Human Cardiac Troponin I: Epitopic Analysis with Synthetic Peptides," *Molecular Immunology*, vol. 29 (2) 271–278 (1992).

Staprans, Ilona, et al., "Skeletal and Cardiac Troponins and Their Components," *J. Biochem.*, vol. 72, (1972), pp. 723–735.

Eisenberg, Evan, et al., "Troponin–Tropomyosin Complex," *The Journal of Biological Chemistry*, vol. 249, No. 15 (1974), pp. 4742–4748.

*Primary Examiner*—Mindy Fleisher
*Assistant Examiner*—Nancy J. Degen
*Attorney, Agent, or Firm*—Fredrikson & Byron, P.A.

[57] ABSTRACT

Stabilized composition of troponin I or T for immunoassays, comprising an aqueous solution containing troponin I or troponin T, 1 to 10 molar equivalents of troponin C per molar equivalent of troponin I or T, and $Mg^{++}$ and/or $Ca^{++}$ ions, as well as a process for stabilizing a composition of troponin I or T for immunoassays consisting in adding from 1 to 10 molar equivalents or troponin C per molar equivalent of troponin I or T.

18 Claims, No Drawings

STABILIZED COMPOSITION OF TROPONIN FOR IMMUNOASSAYS AND PROCESS FOR STABILIZING TROPONIN FOR IMMUNOASSAYS

This application is a continuation of application Ser. No. 08/197,298 filed on Feb. 16, 1994 now abandoned.

The present invention relates to a stabilized composition of troponin used as standard in serum or blood plasma troponin immunoassays.

It is known that troponin is a myofibrillar protein complex consisting of 3 proteins, troponins C, I and T, which triggers the regulation of muscle contraction by $Ca^{2+}$, which contraction results from the interaction of myosin and actin of myofibrils.

When muscle is damaged, whether the cardiac muscle, during a myocardial infarction or the skeletal muscle, during prolonged physical exercise, the contractile proteins then released appear more or less rapidly in the blood stream.

Thus, the determination of troponins for the early diagnosis of myocardial infarction has recently been proposed, whether that of troponin T in Circulation 83 902–912 (1991) or of troponin I in Am. Heart J 110 1333–44 (1987) and Molecular Immunology 29 (2) 271–278 (1992).

Any enzymatic immunoassay or any radioimmunoassay used in pathology laboratories involves, in general, the supply by the manufacturer, in addition to the reagents required for the assay, that is to say labelled or non-labelled antibodies, tracer agents and solutions for dilution, of a standard for the compound to be assayed which, when used under conditions similar to those for the sample to be studied, will serve as reference for calculating the results and/or as positive control.

It is known that proteins are not very stable in solution, and reagents containing them are frequently marketed in freeze-dried form, together with a solvent, of suitable composition, in which the said reagents will have to be dissolved by the user before use; keeping the solutions obtained at 4° C. makes it possible to use them for several days, even if daily calibration shows some variation in the concentrations of the reagent; in general, and this is what is recommended for troponin T, the standard solutions prepared from the freeze-dried product are frozen, in unit dose.

Buffered aqueous solutions of troponin, especially those of troponin I and T, can be stored for several months at –80° C., but is has been observed that they are not stable for more than a few hours at +4° C., even if protease inhibitors or antibacterial agents were added thereto, thereby forcing pathology laboratories to frequently prepare, sometimes twice daily, their solutions for calibration.

The present invention allows storage, for several days at +4° C., of more or less diluted standard solutions of troponin I or troponin T which are used as reference in specific immunoassays.

The stabilized composition of the invention comprises, in aqueous medium, one of the two troponins I or T depending on the assay to be carried out and from 1 to 10 molar equivalents of troponin C and preferably from 2 to 5 equivalents, as well as a large amount of $Mg^{++}$ and/or $Ca^{++}$ ions. The $Mg^{++}$ and/or $Ca^{++}$ ions are present in the form of salts, particularly chloride, bromide or nitrate. The quantity of $Mg^{++}$ and/or $Ca^{++}$ salt, may be 100 to 10,000 times by weight that of troponin I or troponin T.

Troponin C may be of human or animal origin.

The concentration of troponin I or T in the solutions according to the invention correspond to those generally used in immunoassays, as a rule between 0.01 ng/ml and 1 µg/ml and preferably between 0.2 ng/ml and 25 ng/ml, while the concentration of $Mg^{++}$ and/or $Ca^+$ salts, which is not critical, may be between 20 µm and 10 mM; conventionally, this concentration will be close to 2 mM.

The solution may be buffered, in a conventional manner, to a pH of between 4 and 10, preferably 5.5 and 7.5, and the solvent may consist, partially or totally, of normal human plasma, in order to have a standard sample comprising same components as the sample to be studied, which contains the plasma or the serum from the patient.

The subject-matter of the invention is also a powdered troponin I or T composition, preferably in freeze-dried form, optionally comprising $Mg^{++}$ and/or $Ca^{++}$ ions, such as $CaCl_2$, and from 1 to 10 molar equivalents of troponin C, although in this case the presence of troponin C will be useful for ensuring the stability of the other troponins only from the time when the composition will have been dissolved in an aqueous solution by the user.

Possibly, the freeze-dried composition does not contain $Mg^{++}$ and/or $Ca^{++}$ ions. In that case, they are introduced at the dissolution step.

The subject-matter of the invention is also a process for stabilizing a solution of troponin I or T for immunoassays, consisting in adding from 1 to 10 molar equivalents of troponin C per molar equivalent of troponin I or T, and $Mg^{++}$ and/or $Ca^{++}$ ions, for example $CaCl_2$.

In what follows, exemplary embodiments of the invention and the corresponding preservation test results are described.

Human troponin I (TnI) was isolated from a heart by the method described in FEBS Lett. 40 253–257 (1974). The solution obtained can be preserved for several months at –80° C., at a concentration greater than 10 µg/ml in phosphate-buffered saline containing 0.5% casein.

Troponin T (TnT) can be obtained as described in J. Biochem. 72, 723–735 (1972) or in J. Biol. Chem. 249 4742–4748 (1974).

Troponin C (TnC) can be isolated by the method described in Acta Chem. Scand. B 42; 211–215 (1988) from the complex of the 3 troponins (T, C, I), of bovine origin, which is on the market.

The concentrations of the solutions prepared are determined with Bradford reagent, described in Ann. Biochem. 72 248 (1976), and which is marketed; the standard product is a known mixture of troponin I, C and T, marketed by the company SIGMA, freeze-dried, with the reference T 4895.

PREPARATION OF A COMPOSITION ACCORDING TO THE INVENTION

Composition Containing 5 Molecules of Troponin C Per Molecule of Troponin I

276 µg of $CaCl_2, 2H_2O$, 10 µl of troponin I solution at 10 µg/ml and 50 µl of troponin C solution at 10 µg/ml are introduced into 940 µl of $KH_2PO_4$ buffer (0.1M; pH 6.8) containing 10% normal human plasma.

It is preferable to carry out these operations in sterile medium using troponin I and troponin C solutions sterilized for example by passing them through a filter with a pore diameter of 0.22 µm.

The solution obtained, having TnI concentration about 100 ng/ml and TnC concentration about 500 ng/ml, is then used to prepare a series of dilutions from 1 ng/ml to 10 ng/ml of troponin I.

Solutions Containing 1 or 2 or 10 Molar Equivalents of Troponin C Relative to Troponin I are Prepared in the Same Manner The powdered composition can be obtained by freeze-drying an aqueous composition prepared composition prepared as above but without human plasma.

Solutions containing 1 to 10 molar equivalents of troponin C relative to troponin T are prepared in a similar manner by substituting troponin I with troponin T.

Test Procedure

The solutions stored at 4° C. are assayed on the chosen days, over 6 weeks, using standard calibration series, prepared immediately before use, from a troponin I solution preserved at –80° C.

The assay is performed with two monoclonal antibodies directed against the myocardial troponin I; the first antibody is adsorbed onto the walls of immunoassay tubes marketed by NUNC (USA) under the reference Maxisorp, Startube; the second antibody is labelled with peroxidase; the method is a sandwich method.

The preparation of these antibodies is described in Molecular Immunology 29 (2) 271–278 (1992). It was observed that there is no interference in this assay with the other isoforms of troponin I, troponin C or the other myocardial proteins.

In the absence of TnC, from the first day of storage, a substantial decrease in the TnI concentration is observed for all the dilutions; if TnC is replaced with actomyosin or with tropomyosin, at the rate of 5 molar equivalents relative to TnI, the concentration of TnI measured after 12 days is now only ⅔ of that of the starting concentration of 10 ng/ml whereas the solutions stabilized with TnC and $CaCl_2$ are not altered.

After 40 days, the TnI solutions, stabilized with various concentrations of TnC and $CaCl_2$, are not altered, whereas the non-stabilized solutions have an apparent concentration which may fall by up to 80%.

We claim:

1. A standard composition for use in immunoassays comprising an aqueous solution containing troponin I or troponin T at a concentration of 0.01 ng/ml to 1 microgram/ml, 1 to 10 molar equivalents of troponin C per molar equivalent of troponin I or T, and $Mg^{++}$ and/or $Ca^{++}$ ions, wherein the concentration of troponin I or troponin T remains substantially stable for at least one day at 4° C.

2. The composition according to claim 1, wherein the avatity of $Mg^{++}$ and/or $Ca^{++}$ salts is between 100 to 10,000 times by weight of troponin I or troponin T.

3. The composition according to claim 1, comprising troponin I and 2 to 5 molar equivalents of troponin C per molar equivalent of troponin I.

4. The composition according to claim 1 wherein the composition is an aqueous solution buffered to a pH of between 4 and 10.

5. The composition according to claim 1 wherein the composition is an aqueous solution buffered to a pH of between 4 and 6 and wherein the solution comprises up to 100% human plasma.

6. The composition according to claim 1, wherein the concentration of troponin I is between 0.01 ng/ml and 1 µg/ml and the concentration of $Mg^{++}$ and/or $Ca^{++}$ salts is between 20 µM and 10 mM.

7. The composition according to claim 1, containing $CaCl_2$.

8. A method of preparing a standard composition for use in immunoassays, the method comprising the steps of (a) providing a powdered composition containing troponin I or troponin T from 1 to 10 molar equivalents of troponin C per molar equivalent of troponin I or T, and $Mg^{++}$ and/or $Ca^{++}$ ions, and (b) dissolving the powdered composition in a solvent to provide an aqueous solution of troponin I or troponin T at a concentration of 0.01 ng/ml to 1 microgram/ml, whenin the composition remains substantially stable for at least one day at 4° C.

9. The method according to claim 8, comprising the additional step of adding a quantity of $Mg^{++}$ and/or $Ca^{++}$ salts between 100 to 10000 times by weight of troponin I or troponin T.

10. An assay for troponin I or T comprising the steps of (a) providing a standard composition in aqueous solution comprising troponin I or troponin T, 1 to 10 molar equivalents of troponin C per molar equivalent of troponin I or T, and $Mg^{++}$ and/or $Ca^{++}$ ions, wherein the concentration of troponin I or troponin T in solution remains substantially stable for at least one day at 4° C., and (b) determining the level of troponin I or T present.

11. The assay according to claim 10 wherein the assay is an immunoassay.

12. The assay according to claim 1, wherein the standard composition comprises a quantity of $Mg^{++}$ and/or $Ca^{++}$ salts that is between 100 to 10000 times by weight of troponin I or troponin T.

13. The assay according to claim 10, wherein the standard composition comprises troponin I and 2 to 5 molar equivalents of troponin C per molar equivalent of troponin I.

14. The assay according to claim 10, wherein the aqueous solution is buffered to a pH of between 4 and 10.

15. The assay according to claim 10, wherein the aqueous solution is buffered to a pH of between 4 and 6 and comprises up to 100% human plasma.

16. The assay according to claim 10, wherein the concentration of troponin I in the standard composition is between 0.01 ng/ml and 1 µg/ml and the concentration of $Mg^{++}$ and/or $Ca^{++}$ salts is between 20 µm and 10 mM.

17. An assay for troponin I or T comprising the steps of (a) providing a powdered composition containing troponin I or troponin T, from 1 to 10 molar equivalents of troponin C per molar equivalent of troponin I or T, and $Mg^{++}$ /or $Ca^{++}$ ions, and (b) dissolving the powdered composition in a solvent to provide an aqueous solution of troponin I or troponin T at a concentration that remains substantially stable for at least one day at 4° C., and (c) determining the level of tropenin I or T present.

18. A series of dilutions for use as standard compositions in performing an assay for troponin I or T, the series comprising aqueous solutions comprising troponin I or troponin T at a plurality of concentrations between 0.01 ng/ml to 1 microgram/ml, 1 to 10 molar equivalents of troponin C per molar equivalent of troponin I or T, and $Mg^{++}$ and/or $Ca^{++}$ ions, wherein the concentration of troponin I or troponin T in solution remains substantially stable for at least one day at 4° C.

* * * * *